United States Patent [19]

Kato et al.

[11] Patent Number: 4,848,895
[45] Date of Patent: Jul. 18, 1989

[54] AUTOMATIC EYE REFRACTIVE POWER MEASURING APPARATUS

[75] Inventors: Yasuo Kato; Kiwami Horiguchi; Shinji Wada; Ikuo Kitao, all of Tokyo, Japan

[73] Assignee: Tokyo Kogaku Kikai Kabushiki Kaisha, Tokyo, Japan

[21] Appl. No.: 820,793

[22] Filed: Jan. 22, 1986

[30] Foreign Application Priority Data

Jan. 22, 1985 [JP] Japan .................................. 60-10371
Jun. 22, 1985 [JP] Japan ................................. 60-136515

[51] Int. Cl.$^4$ ............................................. A61B 3/10
[52] U.S. Cl. ................................... 351/211; 351/206; 351/205
[58] Field of Search ....................... 351/205, 206, 211

[56] References Cited

U.S. PATENT DOCUMENTS

| | | | |
|---|---|---|---|
| 4,277,150 | 7/1981 | Wada et al. | 351/206 |
| 4,591,247 | 5/1986 | Kamiya et al. | 351/211 |
| 4,626,089 | 12/1986 | Takahashi et al. | 351/206 |
| 4,676,612 | 6/1987 | Wada et al. | 351/205 |
| 4,755,041 | 7/1988 | Ishikawa et al. | 351/211 |

Primary Examiner—Rodney B. Bovernick
Assistant Examiner—P. M. Dzierzynski

[57] ABSTRACT

There is disclosed an automatic eye refractive power measuring apparatus for automatically measuring refractive power of an eye under test by means of objective measurement. It comprises a projection system for projecting a measuring target image to a retina of the eye under test by invisible light; an imaging optical system for imaging a reflection image of the measuring target image projected to the retina and reflected by the retina; an opto-electric detector having a photosensitive surface disposed at imaging position and adapted to output electrical signal corresponding to the measuring target image formed on the photosensitive surface; display device for displaying the measuring target image reflected on the retina based on the electrical signal as a visible image; and an auto-measuring portion adapted to detect focussing state of the measuring target image projected to the retina based on the electrical signal and automatically calculated refractive power of the eye under test from the electrical signal.

5 Claims, 6 Drawing Sheets

AUTOMATIC EYE REFRACTIVE POWER MEASURING APPARATUS

FIELD OF THE INVENTION

This invention relates to an automatic eye refractive power measuring apparatus for automatically measuring refractive power of an eye under test, and more particularly to an automatic eye refractive power measuring apparatus for detecting the focussing state of a measuring target image projected to a retina of the eye under test by an opto-electric detector, indicating the focussing state of the measuring target image by electrical signal outputted from the opto-electric detector, and measuring refractive power of the eye under test.

BACKGROUND OF THE INVENTION

There has been known an automatic eye refractive power measuring apparatus for projecting a measuring target image to the retina of an eye under test by using infrared light as invisible light and automatically measuring the focussing state of the measuring target image. In this type of automatic eye refractive power measuring apparatus, the anterior portion of the eye under test is collimated by a television monitor, etc. in order to position the eye under test.

In the conventional automatic eye refractive power measuring apparatus, the measuring target image is projected on an opto-electric element for detecting only focussing state and no means is provided for a tester himself to observe the measuring target image directly.

Therefore, in the conventional automatic eye refractive power measuring apparatus, even when an adverse affection is exerted on the measuring target image by reflection of the cornea and crystal body, or by reflection light reflected on the eyelashes and eyelid, the tester himself cannot recognize it. Accordingly, the test result lacks dependability. Also, even when accommodation is acted on the eye under test, it is required to be judged from the result of the measurement. Therefore, in order to increase dependability, a high eyesight art of the tester himself is required.

OBJECT OF THE INVENTION

It is therefore a first object of the present invention to provide a highly dependable automatic eye refractive power measuring apparatus, wherein a measuring target image is made as a visible image so that the tester himself can observe it and the tester can always confirm the state of the measuring target image on the retina of the eye under test during the automatic measurement of refractive power of the eye under test.

A second object of the present invention is to provide an automatic eye refractive power measuring apparatus, wherein a measurement application scope can be improved by avoiding inability of measurement due to a decrease in the level of light quantity of the measuring target image on the retina which occurs when the eye under test suffer from a disease such as cataract, the diameter of the pupil of the eye under test is small or the like.

SUMMARY OF THE INVENTION

In order to achieve the above first object, a first embodiment of the invention comprises a projection system for projecting a measuring target image to a retina of the eye under test by invisible light; an imaging optical system for imaging a reflection image of the measuring target image projected to the retina and reflected by the retina; an opto-electric detector having a photosensitive surface disposed at the imaging position and adapted to output an electrical signal corresponding to the measuring target image formed on the photosensitive surface; display means for displaying the measuring target image reflected on the retina based on the electrical signal as a visible image; and an auto-measuring portion adapted to detect the focussing state of the measuring target image projected to the retina based on the electrical signal and automatically calculate refractive power of the eye under test from the electrical signal.

In order to achieve the above second object, a second embodiment of the invention comprises a projection system for projecting a measuring target image to a retina of the eye under test by invisible light; an imaging optical system for imaging a reflection image of the measuring target image projected to the retina and reflected by the retina; an opto-electric detector having a photosensitive surface disposed at the imaging postion and adapted to output an electrical signal corresponding to the measuring target image formed on the photosensitive surface; display means for displaying the measuring target image reflected on the retina based on the electrical signal as a visible image; an auto-measuring portion adapted to detect the focussing state of the measuring target image projected to the retina based on the electrical signal and automatically calculate refractive power of the eye under test from the electrical signal; a manual measurement portion for measuring refractive power of the eye under test by observing the focussing state of the measuring target image through the display means; and measurement mode switching means for selectively switching to the manual measurement portion and the auto-measurement portion.

Since the first invention is such constituted as mentioned above, a measuring target image projected to the retina of the eye under test is detected by an opto-electric detector, the measuring target image is indicated based on the electrical signal outputted from the opto-electric detector, and such information as slit space of an image showing its focussing state is automatically measured. Accordingly, the tester can know whether the measuring target image projected to the retina of the eye under test is affected by something and judge dependability of the measurement result.

That is, according to this automatic eye refractive power measuring apparatus, a comparatively more accurate eyesight test can be carried out. Further, according to the constitution of the first invention, the slit space, etc. indicating focussing state of the measuring target image projected to the retina of the eye under test is measured by using the electrical signal outputted from the opto-electric detector. Accordingly, an opto-electric detector as a detecting portion for measurement and an opto-electric detector for indicating an image are not required to be provided separately. Thus, a simple constitution of the apparatus is obtainable.

According to the constitution of the second embodiment of the invention, not only auto-measurement but also manual measurement in which the tester observes the measurement target image of the display means can be effected. Accordingly, even if such an instance should arise as inability of measurement due to shortage of light quantity of the measuring target image projected on the retina caused by disease or the like of the patient, manual measurement can be easily carried out by simply switching the measuring mode without using additional measuring apparatuses. Accordingly, the measurement applicable scope can be enlarged.

DESCRIPTION OF THE PREFERRED EMBODIMENTS

Figure 1:
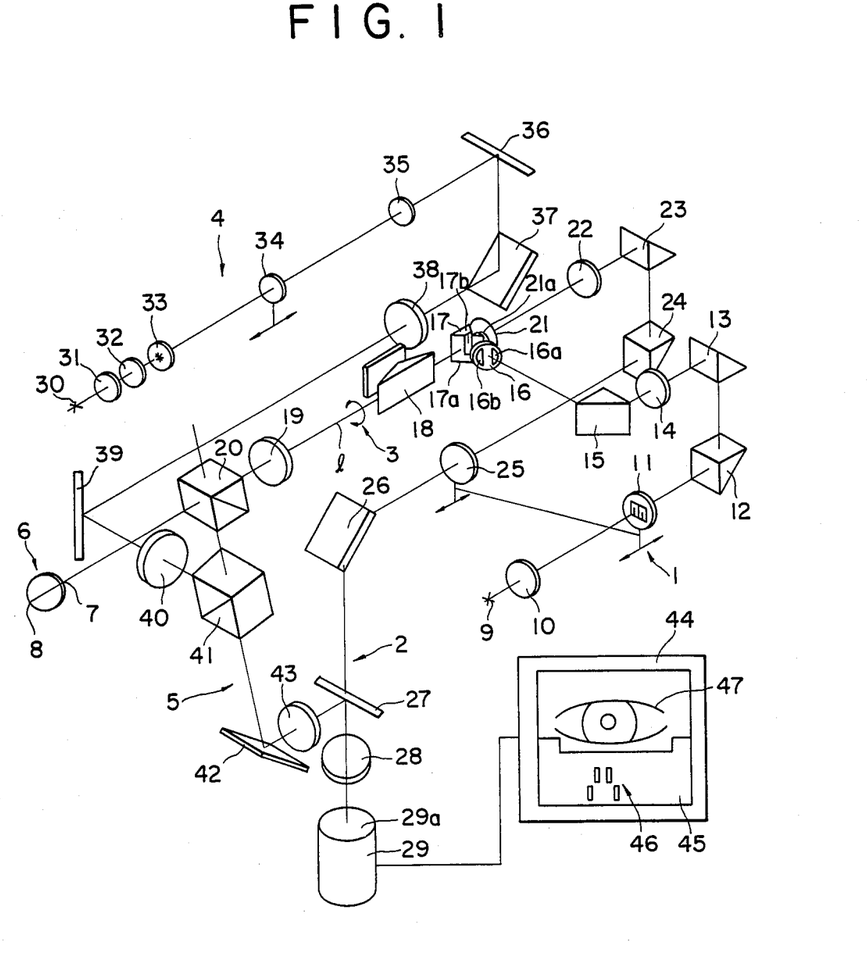
FIG. 1 is a schematic constitution of an optical system of an automatic eye refractive power measuring apparatus according to the present invention.

FIG. 1 illustrates an optical system of an automatic eye refractive power measuring apparatus according to the present invention.

In FIG. 1, 1 denotes a target image projection system, 2 denotes an imaging optical system, 3 denotes a common use optical system commonly used for both the target image projection system 1 and the imaging optical system 2, 4 denotes a chart projection system, 5 denotes a sighting optical system, 6 denotes an eye under test, and 7 denotes an anterior portion.

Figure 2:
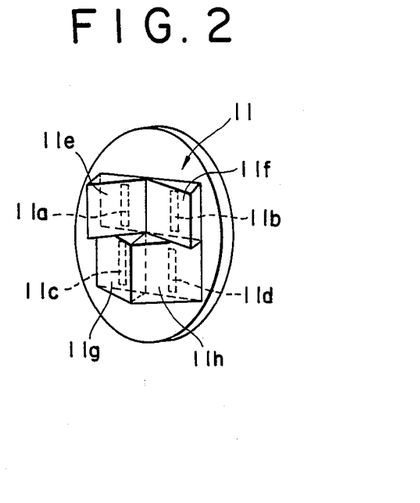
FIG. 2 is a perspective view of a target plate constituting the optical system.

The target image projection system 1 has such a function as to form a target image on a retina 8 by projecting target light to the retina 8 of the eye 6 under test through the common use optical system 3. The target image projection system 1 generally comprises a luminous element 9, a condenser lens 10, a target plate 11, reflection prisms 12, 13, a relay lens 14, a reflection prism 15, and a half moon diaphragm plate 16. In this embodiment, the luminous element 9 emits infrared light as invisible light. The infrared light becomes a parallel bundle of rays by the condenser lens 10 to illuminate the target plate 11. The target plate 11, as shown in FIG. 2, is formed with slits 11a through 11d and attached with four deflection prisms 11e through 11h. Due to the foregoing, the target plate 11 is illuminated by the infrared light to form measuring target light. At this time, the deflection prisms 11e through 11h deflects the measuring target light to a direction perpendicular to the longitudinal direction of the slits.

The common use optical system 3 comprises a slit prism 17, an image rotator 18, an objective lens 19, and a beam splitter 20. The measuring target light from the target plate 11 is reflected by the reflection prisms 12, 13, 15, guided to the half moon diaphragm plate 16, passes through half moon holes 16a, 16b, and reflected on a reflection surface 17a of the split prism 17. The measuring target light reflected on the reflection surface 17a passes the pupil of the eye 6 under test through image rotator 18, objective lens 19 and beam splitter 20, and is projected on the retina 8.

The half moon diaphragm 16 is disposed in such a manner as to be in a conjugate relation with the pupil position of the eye 6 under test in a proper position with respect to the objective lens 19. The half moon diaphragm 16 is adapted to block harmful reflection light for measurement from the anterior portion 7 of the eye 6 under test and enter the target light to the eye 6 under test. The image rotator 18 is adapted to rotate the measuring target image formed on the retina 8 by angle $\theta$ in the meridian direction of the eye 6 under test by rotating it about an optical axis 1 of the common use optical system 3 by angle of $\theta/2$.

The reflection light of the measuring target image projected on the retina 8 is guided to the imaging optical system 2 through beam splitter 20, objective lens 19, slit hole 17a of the slit prism 17, and opening 21a formed in the central portion of an opening diaphragm plate 21, relay lens 22 and reflection prism 23. The opening diaphragm 21 is disposed in a conjugate position with the pupil of the eye 6 under test and adapted to guide the reflection light passing through the central portion of the pupil to the relay lens 22.

The imaging optical system 2 generally comprises a reflection mirror 24, a movable lens 25, a reflection mirror 26, a half mirror 27, and an imaging lens 28. The imaging optical system 2 is adapted to guide the reflection light of the measuring target image formed on the retina 8 to a photosensitive surface 29a of a photosensitive apparatus 29 as an opto-electric detector and forms a measuring target image thereon. In this embodiment, if the image rotator 18 is rotated about the optical axis 1 by angle of $\theta/2$ as mentioned above, the measuring target image is rotated by angle of $\theta$ in its rotating direction. However, since the reflection light reflected on the retina 8 passes through the image rotator 18 again, it causes the measuring target image to rotate by angle of $\theta$ in the opposite direction with respect to the rotating direction of the image rotator 18 and the photosensitive surface 29a of the image pick-up apparatus 29 is formed with a measuring target image facing toward a predetermined direction irrespective of the rotation of the image rotator 18.

Figure 3:
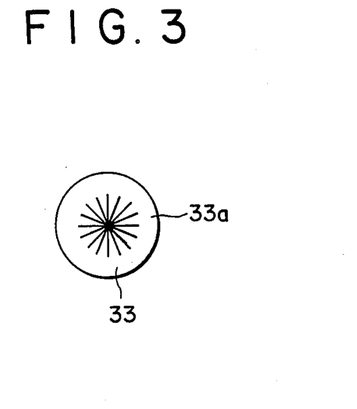
FIG. 3 is a plan view of a chart plate constituting the optical system.

The chart projection system 4 generally comprises a tungsten lamp 30 as visible light source, a condenser lens 31, a color correction filter 32, a chart plate 33, a movable lens 34, reflection mirrors 36, 37, a relay lens 38, a reflection mirror 39, and an objective lens 40. In this embodiment, the chart plate 33 is illuminated by the tungsten lamp 30 through the condenser lens 31 and the color correction filter 32. The light emitted from the tungsten lamp 30 has a selected wavelength determined by the color correction filter 32 and only visible light of the range from 400 nm to 700 nm is permitted to pass through the color correction filter 32. The chart plate 33 is formed with a chart 33a shown in FIG. 3 and the light passed through the chart 33a is guided to the movable lens 34 and the relay lens 38. The light guided to the relay lens 38 is shifted by the reflection mirrors 36, 37, and 39, and passes through the relay lens 38 and the objective lens 40, guided to the beam splitter 41 and projected toward the eye 6 under test through the beam splitter 20.

The movable lens 34 is disposed in such a manner as to be movable in its optical axis. In objective measurement, the movable lens 34 is disposed in a position from where the eye 6 under test is far sighted or foggy sighted corresponding to refractive power of the eye 6 under test, so that the measurement can be carried out in the state that the accommodation of the eye 6 under test is removed.

The anterior portion 7 of the eye 6 under test is illuminated by an illumination lamp (not shown), and the image of the anterior portion 7 of the eye 6 under test is formed on the photosensitive surface 29a of the image pick-up apparatus 29 by the sighting optical system 5. The reflection bundle of rays reflected from the anterior portion 7 of the eye 6 under test is reflected by the beam splitters 20, 41 and a reflection mirror 42. The reflection bundle of rays reflected by the reflection mirror 42 passes through an imaging lens 43, the half mirror 27 and the image pick-up lens 28, guided onto the photosensitive surface 29a of the image pick-up apparatus 29, and an image of the anterior portion is formed on the photosensitive surface 29a of the image pick-up apparatus 29.

The image pick-up apparatus 29 is connected to a television monitor 44, and 45 denotes a display surface. On the display surface 45 is displayed a measuring target image formed on the photosensitive surface 29a as a visible image based on electrical signal from the image pick-up apparatus 29. In FIG. 1, 46 denotes a measuring target image formed by the imaging optical system 2, and 47 denotes an anterior portion image formed by the sighting optical system 5.

Figure 4:
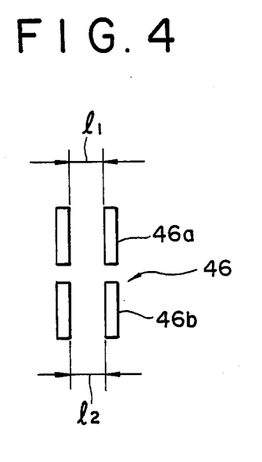
FIGS. 4 through 6 are schematic views showing various types of imaging state of a measuring target image formed by the optical system.
Figure 5:
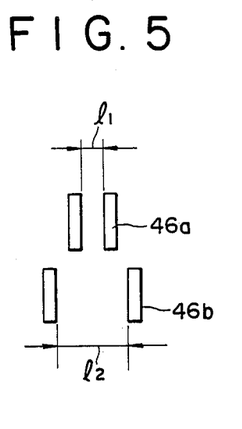
Figure 6:
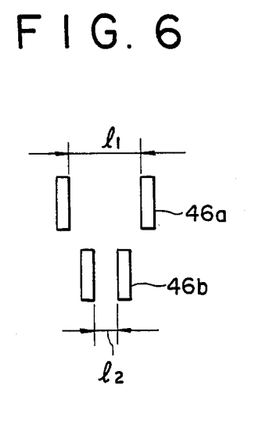

In this embodiment, when the target image 46 displayed on the display surface 45 of the television monitor 44 is focused on the retina 8, the target image 46 is in agreement in the space $l_1$ between a pair of target images 46a at its upper portion and the space $l_2$ between a pair of target images 46b at its lower portion as shown in FIG. 4. For example, when the measuring target image is focused at a front portion of the retina 8, the space $l_1$ is smaller than the space $l_2$ as shown in FIG. 5. On the other hand, when the measuring target image is focused at a rear portion of the retina 8, the space $l_1$ is larger than the space $l_2$ as shown in FIG. 6.

In measurement of the refractive power, the target plate 11 is moved in such a manner as to bring both the spaces $l_1$, $l_2$ of the measuring target image in alignment with respect to each other. The refractive power is obtained by the moving quantity at that time. In this embodiment, the movable lens 25 is integrally actuated while maintaining the conjugate relation with the target plate 11.

Figure 7:
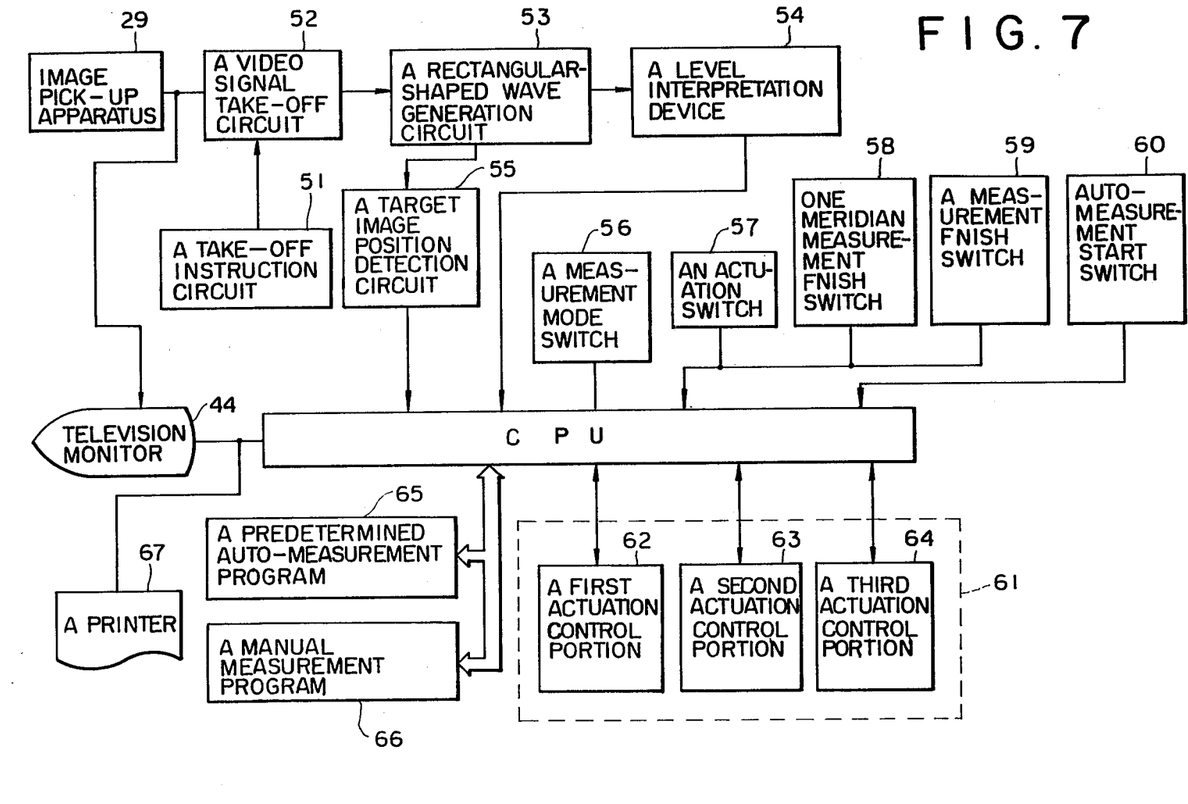
FIG. 7 is a measurement circuit for actuating the automatic eye refractive power measuring apparatus.

Next, a measurement circuit shown in FIG. 7 will be described.

The electrical signal of the image pick-up apparatus 29 is partly inputted in the television monitor 44 to display the image of the anterior portion. The remaining part of the electrical signal is inputted in an electrical signal take-off circuit 52, so that the electrical signal regarding the measuring target image is taken off based on take-off instruction signal of a take-off instruction circuit 51. Such taken off electrical signal is inputted in a rectangular-shaped wave generation circuit 53, and the wave shape thereof is treated and converted to a predetermined rectangular-shaped wave. The rectangular-shaped wave is inputted in a level interpretation device 54 and a target image position detection circuit 55. The electrical signal level interpretation device 54 interprets luminous level of the rectangular-shaped wave. Due to the foregoing, light quantity level of the measuring target image 46 is detected. The target image position detection circuit 55 is adapted to detect signal space of the rectangular-shaped wave signal corresponding to the space of the measuring target image 46.

In this embodiment, output signal outputted from the electrical signal level interpretation device 54 and the target image position detection circuit 55, or respective signals as will be described later is processed by CPU 50 as a micro computer.

CPU 50 controls a measurement mode switch 56 for switching from an auto-measurement to a manual measurement, an actuation switch 57 for moving the target plate 11 and the movable lens 25, a one meridian measurement finish switch 58 for emitting the instruction signal every time measurement of one meridian is finished, a measurement finish switch 59 for emitting the instruction signal when measurement of all meridians are finished, and an auto-measurement start switch 60 for starting auto-measurement, respectively. In addition, CPU 60 controls an actuation control portion 61. The actuation control portion 61 comprises a first actuation control portion 62 for moving the target plate 11 and the movable lens 25 along the optical axis, a second actuation control portion 63 for rotating the image rotator 18 about the optical axis, and a third actuation control portion 64 for moving the movable lens 34 of the chart projection system 4 along the optical axis. CPU 50 runs a predetermined auto-measurement program 65 or a manual measurement program 66 which are built therein beforehand. Respective measurement results are recorded by a printer 67 in order.

Figure 8:
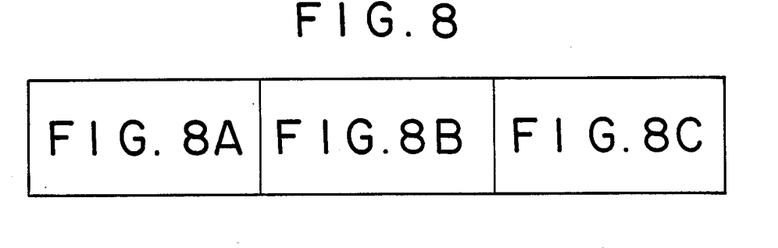
FIGS. 8(a) through 8(c) are flow charts for running a program by the measurement circuit.
Figure 8A:
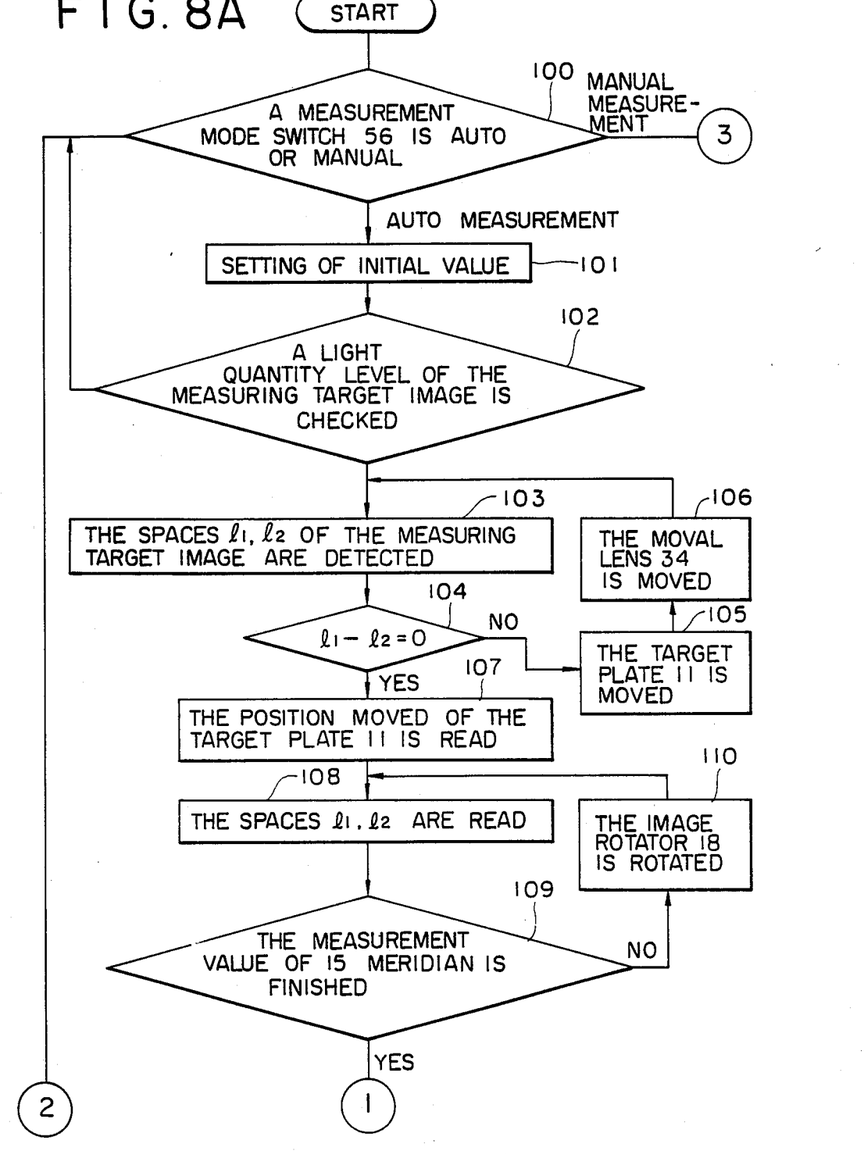
Figure 8B:
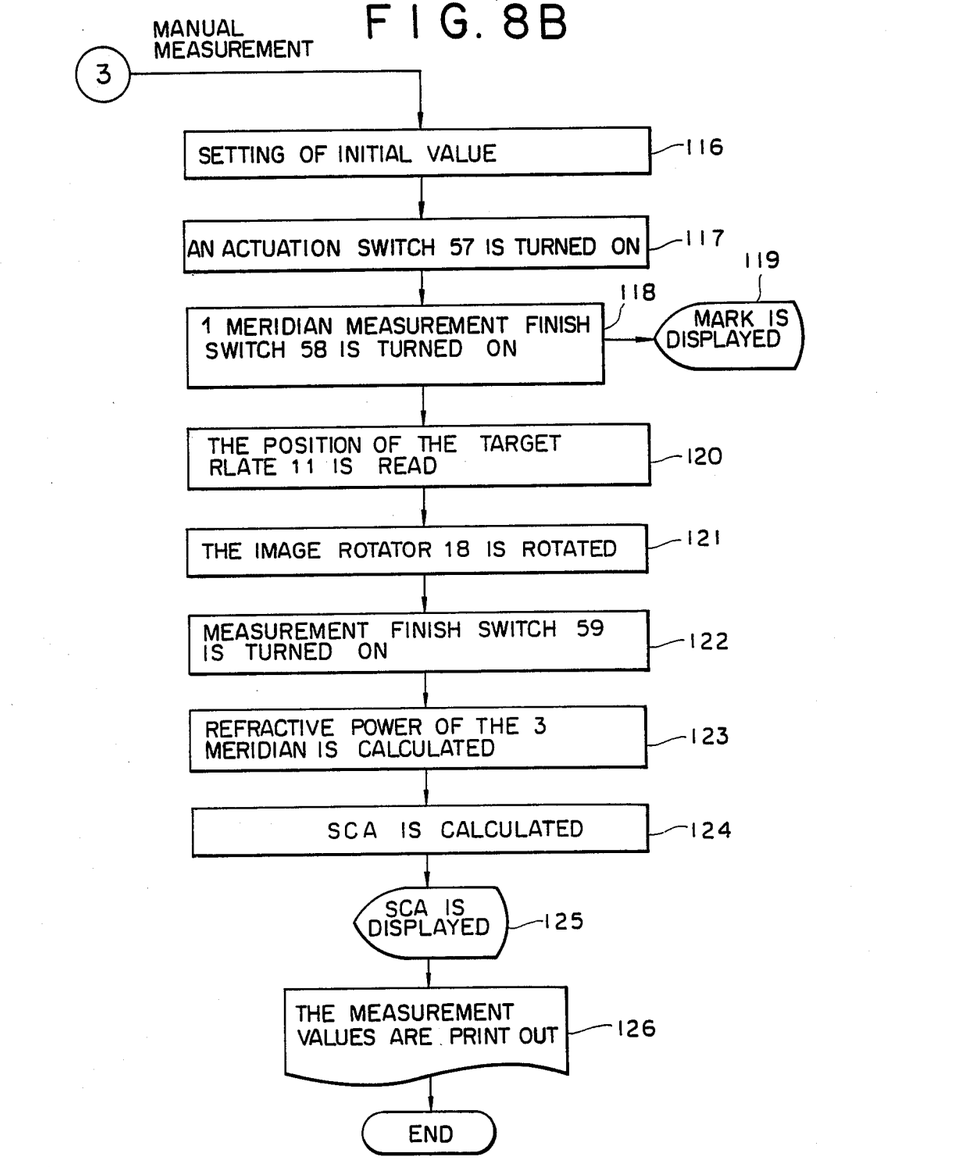
Figure 8C:
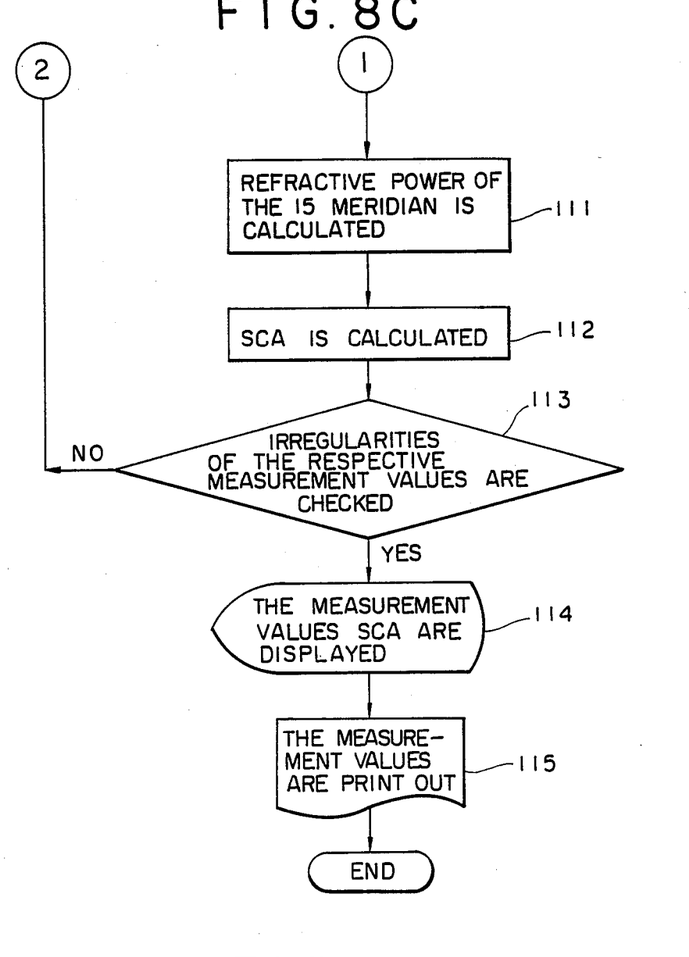

Next, operation of the eye refractive power measuring apparatus of this constitution will be described with reference to a flow chart of FIG. 8.

First of all, when calculative operation of CPU 5 is started upon charging of an electric power source, etc., a switch-over state of the mode switch 56 is interpreted in STEP 100. In the case the mode switch 56 is switched over to the auto-measurement side, CPU 50 calls the auto-measurement program 65, and the following measurement is carried out based on the foregoing.

First, upon setting of an initial value in STEP 101, the target plate 11 is brought to "zero diopter position" by the first actuation control portion 62, the image rotater 18 is brought to "zero degree" position by the second actuation control portion 63, and the movable lens 34 is moved to "zero diopter" position by the third actuation control portion 64.

Next, a light quantity level of the measuring target image 46 is checked by the electrical signal level interpretation device 54 based on electrical signal of the image pick-up device 29 in STEP 102. When the light quantity level of the measuring target image is interpreted that it does not reach the predetermined level yet here, the mode switch 56 is automatically switched to the manual measurement mode side according to the instruction of CPU 50. On the other hand, in the case the light quantity level exceeds the predetermined level, the spaces $l_1$, $l_2$ of the measuring target image are detected based on output of the target image position detection circuit 55 (STEP 103).

When the spaces $l_1$, $l_2$ are detected, CPU 50 calculates the difference of the spaces $l_1-l_2$ and the target plate 11 and the movable lens 25 is integrally moved along the optical path until the difference of the spaces $l_1-l_2$ becomes "zero", that is, until the measuring target image 46 is brought to the focussing position onto the retina 8. In association with the foregoing movement, the movable lens 34 of the chart projection system 4 is moved (STEPS 103 through 106), so that the foggy state of the eye 6 under test is maintained. And, when the difference of the spaces $l_1-l_2$ becomes "zero", the position moved of the target plate 11 is read in (STEP 107), and the refractive power of the "zero degree" meridian direction is obtained based on the moved position.

Next, the image rotator 18 is rotated, for example, 15 times per every "six powers" in the meridian direction to be measured with the position of the target plate 11 held stationary, and the differences of the spaces $l_1-l_2$ corresponding to the respective rotating position are read in (STEPS 108 through 110). The refractive power "$D\theta$" in the "$\theta$" direction can be obtained by calculating the sum of the diopter value corresponding to the stop position of the target plate 11 and the diopter value corresponding to the value of the difference of the spaces $l_1-l_2$. And, there is a relation as shown by the following formula (1) among spherical power A, astigmatism power B and astigmatism axis.

$$D\theta = A + B \cos(\theta - \alpha) \tag{1}$$

Accordingly, based on the refractive powers "$D\theta_1$ through $D\theta_{15}$" obtained in the respective meridian directions (15 meridian directions), the spherical power A, astigmatism power B and astigmatism axis $\alpha$ are calculated respectively based on the method for least squares (STEPS 111, 112).

Next, such obtained calculation result is compared with the measurement value and checking is made whether irregularities of the respective measurement values are within a predetermined range (STEP 113).

When the irregularities of the measurement values are found to exceed the predetermined range by the foregoing checking, the mode switch 56 is automatically switched over to the manual measurement mode according to the instruction of CPU 50.

On the contrary, when the irregularities are within the predetermined range, the measurement values are displayed on the television monitor 44 and at the same time the measurement values are printed by the printer 67 (STEPS 114, 115), and the processing of the auto-measurement-program is terminated.

According to this apparatus, since the display surface 45 of the television monitor 44 displays both the anterior portion image 47 and the measuring target image 46, the tester can observe the state in which the measurement is being carried out.

Next, there will be described on a case where the mode switch 56 was switched over to the manual measurement mode side either manually or automatically. In this case, CPU 50 runs the manual measurement program.

First, in STEP 116, an initial setting like STEP 101 of the aforementioned auto-measurement mode is effected. Next, the tester turns on the actuation switch 57 until both the spaces $l_1$, $l_2$ of the measuring target image as shown in FIG. 4 and integrally moves the target plate 11 and the movable lens 25 along the optical axis while observing the measuring target image on the display surface 45 of the television monitor 44 (STEP 117). Upon finish of this movement, the tester turns on the 1 meridian measurement finish switch 58 to cause CPU 50 to read in the moving position of the target plate 11. The moving position corresponds to the refractive power in the "zero degree" meridian direction the same as in the case of the auto-measurement.

In this case, when the 1 meridian finish switch 58 is turned on (STEP 118), a piece of * mark, for example, indicating the number of measurement is displayed on the television monitor 44 (STEP 119), the position of the target plate 11 is read in (STEP 120), and at the same time, the image rotator 18 is rotated by a predetermined angle (STEP 121). Next, the tester turns on the actuation switch 57 to move the target plate 11 while observing the measuring target image displayed on the television monitor 44 and operation such as reading-in of the moving position is repeated as in the same manner as the above mentioned STEP. At this time, every time one measuring operation is finished, one piece of * mark is displayed on the television monitor 44. And, when at least three measuring operations are effected, the measurement finish switch 59 is turned on to finish the measuring operation (STEP 122). The number of measurements is decided in advance without providing the measurement finish switch 59, so that the measurement will be automatically finished after the predetermined number of measurements are finished.

According to the three times measuring operation, the refractive power in the 3 meridian directions can be obtained (STEP 123), the spherical power A, astigmatism power B and astigmatism axis $\alpha$ are obtained respectively based on the aforementioned formular (1) according to the method for least squares (STEP 124). And, the measuring results of the spherical power A, astigmatism power B and astigmatism axis $\alpha$ are displayed on the television monitor and at the same time, they are printed out by the printer 67 (STEPS 125, 126).

What is claimed is:

1. An automatic eye refractive power measuring apparatus for automatically measuring refractive power of an eye under test by means of objective measurement comprising:

a projection system for projecting by invisible light a measuring target image to the retina of the eye under test;

an imaging optical system for imaging at an imaging position a reflection image of the measuring target image projected to the retina and reflected by the retina;

an opto-electric detector having a photosensitive surface disposed at said imaging position and adapted to output an electrical signal corresponding to the reflection image of a measuring target image formed on the photosensitive surface;

display means for converting the reflection image of a measuring target image to a visible image in accordance with said electrical signal and for displaying the converted visible image;

computer means, selectively operable to one of a fully automatic measurement mode and a manual measurement mode in accordance with the light intensity of said reflection image, for calculating the refractive power of the eye under test in accordance with said electrical signal;

a manual measurement means for measuring the refractive power of the eye under test by observing the focussing state of the measuring target image through said display means;

measurement mode switching means for selectively activating said manual measurement mode and said automatic measurement mode of said computer means in accordance with the light intensity of said reflection image of said measuring target image; and whereby in the automatic measurement mode, the focussing state of the measuring target image projected on the retina is determined based on said electrical signal, and the refractive power of the eye under test is automatically calculated based on said focussing state, while in the manual measurement mode, the operator observes the measuring target image on said display means and manually activates said computer means to calculate the refractive power of the eye under test in accordance with the observed focussing state of said measuring target image.

2. An automatic eye refractive power measuring apparatus according to claim 1, wherein said measurement mode switching means may be manually activated by the operator.

3. An automatic eye refractive power measuring apparatus according to claim 1, wherein said measurement mode switching means is automatically selectively activated by said computer means in accordance with the light intensity of said reflection image.

4. An automatic eye refractive power measuring apparatus according to claim 1, wherein said measurement mode switching means automatically activates said manual measurement mode of said computer means when the light intensity of the measuring target image is less than a predetermined level.

5. An automatic eye refractive power measuring apparatus according to claim 1, wherein in said manual measurement mode, said computer means stores the measured focussing state at a first predetermined meridian by a measurement finish switch at the predetermined meridian and the apparatus further includes means for rotating said measuring target image relative to the eye to measure the focussing state of the measuring target image along a second predetermined meridian.

* * * * *